United States Patent
Wolter et al.

(10) Patent No.: US 9,353,226 B2
(45) Date of Patent: May 31, 2016

(54) COMPOUNDS CONTAINING (METH)ACRYLATE GROUPS AND SULFONATE OR SULFATE GROUPS, POLYMERS AND CONDENSATES MADE THEREFROM AND USE OF THE POLYMERS AND CONDENSATES

(75) Inventors: Herbert Wolter, Tauberbischofsheim (DE); Mona Seyfried, Würzburg (DE); Somchith Nique, Eisingen (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 0 days.

(21) Appl. No.: 14/122,698

(22) PCT Filed: May 24, 2012

(86) PCT No.: PCT/EP2012/059671
§ 371 (c)(1),
(2), (4) Date: Nov. 27, 2013

(87) PCT Pub. No.: WO2012/163781
PCT Pub. Date: Dec. 6, 2012

(65) Prior Publication Data
US 2014/0088279 A1  Mar. 27, 2014

(30) Foreign Application Priority Data

May 27, 2011 (DE) .......................... 10 2011 050 672
May 27, 2011 (EP) ...................................... 11167853

(51) Int. Cl.
*A61K 6/00* (2006.01)
*C08G 77/18* (2006.01)
(Continued)

(52) U.S. Cl.
CPC .............. *C08G 77/18* (2013.01); *A61K 6/0023* (2013.01); *C07F 7/184* (2013.01); *C08G 77/28* (2013.01); *C08G 77/392* (2013.01); *C09J 4/00* (2013.01); *C09J 183/08* (2013.01); *C08G 77/20* (2013.01)

(58) Field of Classification Search
CPC ....... A61K 6/0023; C08G 77/18; C08G 77/28
USPC ....................................... 528/30, 32; 536/279
See application file for complete search history.

(56) References Cited

U.S. PATENT DOCUMENTS 3,328,449 A  6/1967 Haluska
3,748,132 A  7/1973 Arcesi et al.
(Continued)

FOREIGN PATENT DOCUMENTS

CA  2296227 A1  7/2000
DE  10018405 A1  10/2011
(Continued)

OTHER PUBLICATIONS

STN Search Results, Mar. 24, 2015.*
(Continued)

*Primary Examiner* — Vu A Nguyen
(74) *Attorney, Agent, or Firm* — Gudrun E. Huckett

(57) ABSTRACT

The invention relates to a compound, comprising at least three functionalities, that is (a) a sulfonate or sulfate group of the formula —$(O)_d$—$SO_3M$ with d=0 or 1 and M=hydrogen or a monovalent metal cation or the corresponding fraction of a polyvalent metal cation, (b) a (meth)acryl group, and (c) either (c1) at least one further (meth)acryl group or an inorganically condensable group, and/or (c2) a further carboxylic acid function, and/or (c3) a function which increases the refractive index of a material produced from the compounds, that is a thioether group, with the proviso that a sulfonate or sulfate group and a (meth)acrylate group are separated from one another in a silicon-free compound via a hydrocarbon-containing group, the carbon chain of which is either interrupted by O, S or NH or contains a linking group.

34 Claims, 2 Drawing Sheets

(51) Int. Cl.
  *C08G 77/28* (2006.01)
  *C08G 77/392* (2006.01)
  *C09J 4/00* (2006.01)
  *C09J 183/08* (2006.01)
  *C07F 7/18* (2006.01)
  *C08G 77/20* (2006.01)

(56) References Cited

U.S. PATENT DOCUMENTS

| | | |
|---|---|---|
| 4,503,242 A | 3/1985 | Plueddemann |
| 4,777,277 A | 10/1988 | Colas et al. |
| 5,427,706 A | 6/1995 | Kobayashi et al. |
| 5,717,125 A | 2/1998 | Wolter et al. |
| 5,756,767 A | 5/1998 | Wolter |
| 5,792,881 A | 8/1998 | Wolter et al. |
| 5,917,075 A | 6/1999 | Wolter |
| 6,124,491 A | 9/2000 | Wolter et al. |
| 6,447,907 B1 | 9/2002 | Wolter et al. |
| 6,759,449 B2 | 7/2004 | Kimura et al. |
| 6,777,521 B1 | 8/2004 | O'Lenick, Jr. |
| 2002/0119426 A1 | 8/2002 | Jia et al. |
| 2003/0055124 A1 | 3/2003 | Klee et al. |
| 2003/0187094 A1 | 10/2003 | Klee et al. |
| 2004/0138490 A1 | 7/2004 | Wolter |
| 2008/0187499 A1 | 8/2008 | Wolter et al. |
| 2008/0194730 A1 | 8/2008 | Klee et al. |

FOREIGN PATENT DOCUMENTS

| | | |
|---|---|---|
| EP | 1 421 927 A1 | 5/2004 |
| EP | 1 767 523 A1 | 3/2007 |
| WO | 2006/122074 A1 | 11/2006 |
| WO | 2012/019704 A1 | 2/2012 |

OTHER PUBLICATIONS

Kerr R. L. et al.: New type of Li ion conductor with 3D interconnected nanopores via polymerization of a liquid organic electrolyte-filled lyotropic liquid-crystal assembly; J. Am. Chem. Soc. 2009, 131, 15972-15973; see international search report.

Sieburth S. Macn. et al.: A practical synthesis of difunctional organosilane reagents and their applications to the Diels-Alder reaction; J. Org. Chem. 1999, 64, 1780-1781; see international search report.

Xu V. et al.: Heterogenous catalysis using a nanostructured solid acid resin based on lyotropic liquid crystals; J. Am. Chem Soc. 2004, 126, 1616-1617: see international search report.

* cited by examiner

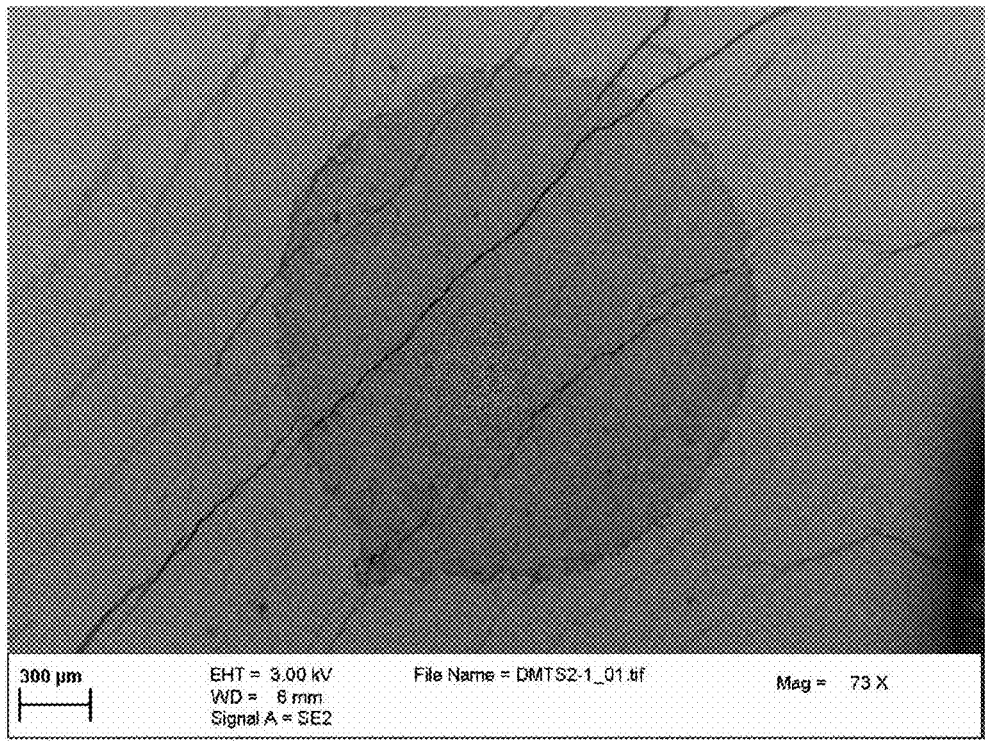
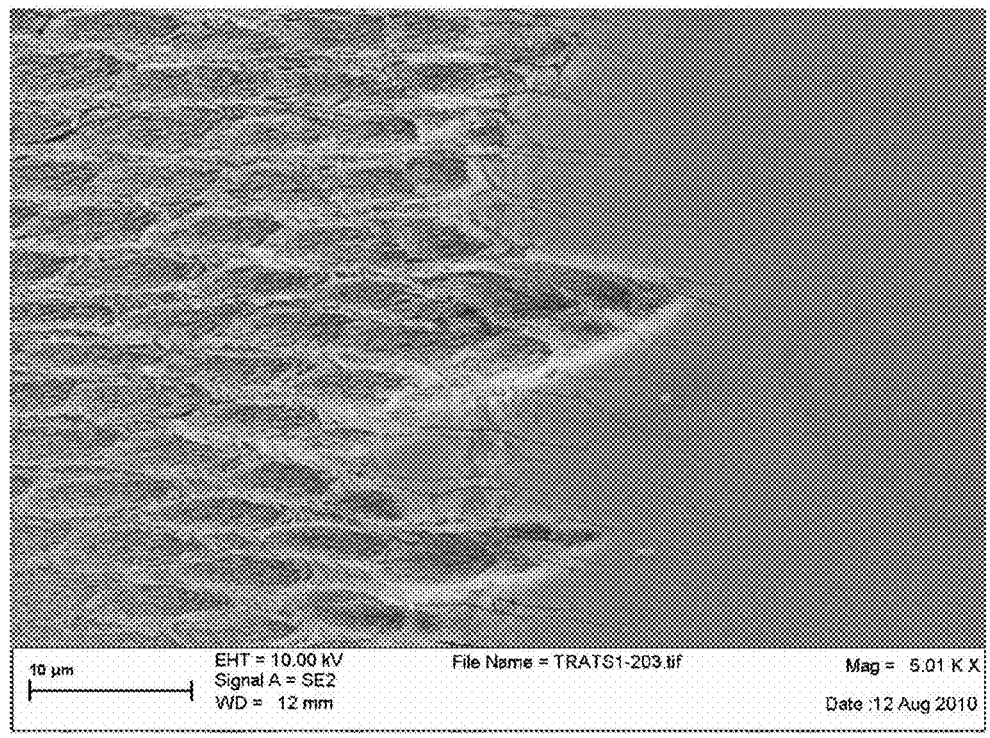
Figure 1a: REM images at different enlargements

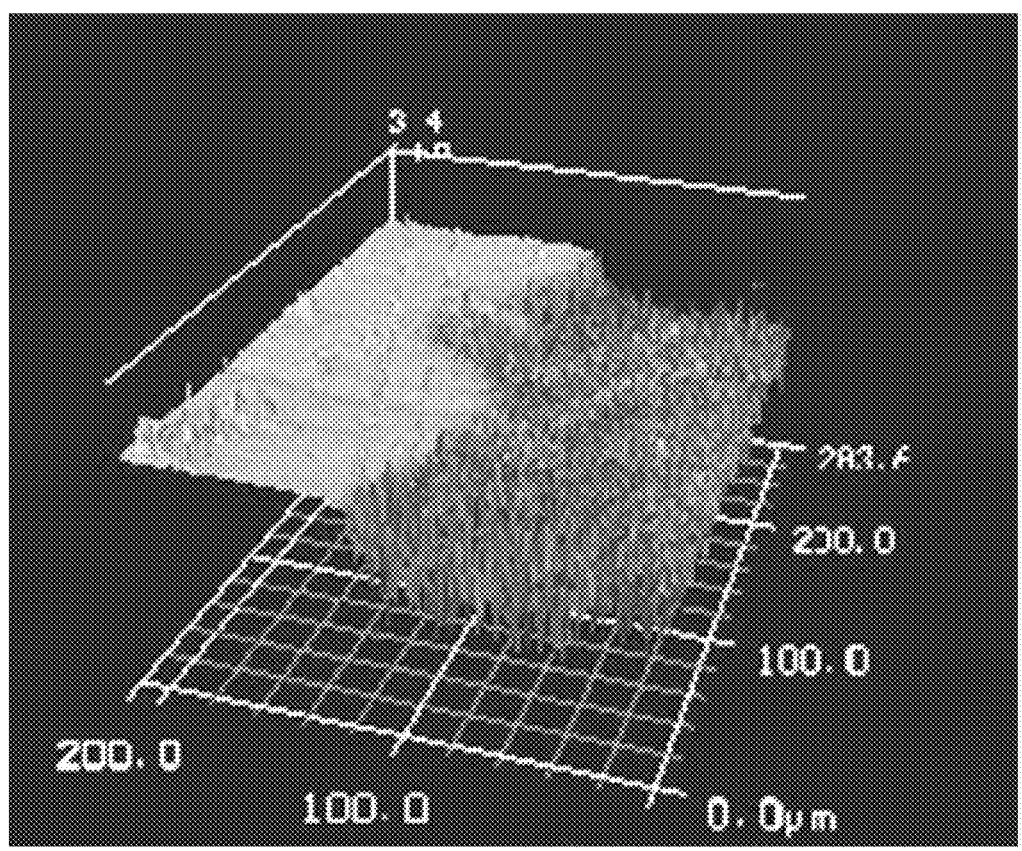
Figure 1b: Profilometer image

COMPOUNDS CONTAINING (METH)ACRYLATE GROUPS AND SULFONATE OR SULFATE GROUPS, POLYMERS AND CONDENSATES MADE THEREFROM AND USE OF THE POLYMERS AND CONDENSATES

BACKGROUND OF THE INVENTION

The present invention concerns compounds with at least one (meth)acryl residue, at least one sulfonate or sulfate group as well as a further, usually reactive group, their polymerization products as well as the use of the monomers and the polymers in the medical field, in particular in dentistry. Inasmuch as the invention concerns silane compounds, it also encompasses the condensates available from them as well as their use.

Polymerizable organic compounds with acid groups are important components for medical products for achieving desired material properties like wetting, etching effect, complexing, and thereby adhesion on biological interfaces. Dental adhesives are based on such conventional monomeric compounds, but exhibit still some considerable deficits. An essential problem in this context is that the etching effect is often insufficient within the context of self-etch application for realizing the necessary retentive structures required for the adhesion and thus a long-lasting connection between dental tissue and restoration material. Therefore, a prior separate etching step with an etching gel cannot be avoided; this, in turn, increases the susceptibility for errors and the treatment costs. Concerning the increasing demands in regard to biocompatibility (reference is being had to the allergy discussion in connection with dental monomers), the above systems also offer no solution. Since the components of the adhesive in case of a restoration come closest to the tooth roots as well as blood vessels, it is of special interest from a toxicological viewpoint to provide systems that are free of monomers.

In the patent application DE 44 16 857 C1, carboxylic acid-functionalized (meth)acrylate alkoxysilanes are described. They are characterized by a plurality of possibilities for varying or adjusting the properties of the inorganic-organic composite polymers produced therefrom. As a result of the contained carboxylic acid groups, additional reaction possibilities (e.g., glass ionomer reactions) as well as an improved adhesion on inorganic surfaces arise. The etching effect (see self-etch application) of a carboxylic acid group is however nowhere as strong as it is sometimes desired. The same holds true for the phosphonic acid-based systems disclosed in EP 1 377 628 B1. Therefore, up to now, it is not possible to obtain with hybrid polymer-based systems a stable enough connection between dental tissue and restoration material in the context of the desirable self-etch application.

For several application purposes, like the stabilization of aqueous silicates or the production of electro-viscous liquids, emulsifiers, detergents or foaming agents, monomeric or condensed silanes containing sulfonate or sulfate groups have been developed. Thus, U.S. Pat. No. 6,777,521 discloses silicone sulfate polymers which are obtainable by the reaction of suitable epoxy compounds with metal sulfate. U.S. Pat. No. 3,328,449 discloses sulfopropylated organo-functional silanes and siloxanes which can be obtained by means of reacting sultones. Organo siloxane sulfosuccinates in which a sulfonated succinic acid ester is bonded by the oxygen atom of the ester group by an alkylene group to a silicon atom are disclosed in U.S. Pat. No. 4,777,277. The preparation of a hydrolytically condensable bis-sulfosuccinate amide of a diaminosilane, obtained by the reaction of the free carboxylic acid of the corresponding succinate amide with sodium sulfite, is disclosed in example 1 of U.S. Pat. No. 4,503,242. A silane which carries a sulfonate group and a hydroxyl group at an alkylene oxyalkylene residue of the silicon is disclosed in U.S. Pat. No. 5,427,706.

The use of purely organic monomers which carry a terminal sulfonate group as well as an unsaturated olefinic group for concurrent etching and base-coating ("priming") of teeth is suggested in US 2002/0119426 A1. The employed AMPS (2-acrylamido-2-methylpropane sulfonic acid) is a commercially available product. U.S. Pat. No. 6,759,449 B2 also discloses dental adhesive compositions which carry an organically polymerizable (meth)acrylic acid group as well as an acidic group. In this context, no distinction is made between sulfonate groups and phosphonate groups or other acidic groups concerning the usability of the compounds and their properties. The same holds true for US 2003/0055124 A1; only for the (meth)acrylamido phosphonic acids, but not for the also disclosed corresponding sulfonic acids, information is provided for the preparation. Another application, US 2008/0194730, essentially by the same group of inventors, suggests again for dental composites the use of self-etch polymerizable N-substituted (meth)acrylic acid amide monomers which carry additionally an acidic unit, selected from phosphonic acid units and sulfonic acid units. N-methacryloyl aminoalkyl sulfonic acids can be used according to the disclosure of EP 1 421 927 A1 as self-etch primers for dental purposes.

DE 102 06 451 A1 discloses dental adhesive compositions from acidically polymerizable nanoparts in an aqueous phase. The nanoparticles consist of siloxanes having acidic as well as organically polymerizable groups bonded thereto. The acidic groups can be either phosphonate groups or sulfonate groups; individual specific advantages for one or the other group are not specified. The only example of use discloses a specific adhesion value of a dental adhesive, made from a phosphonic acid-containing material, on a tooth surface. A process for producing sulfonate group-containing silanes is neither mentioned generally nor in regard to the illustrated compounds.

There is a need for organically polymerizable monomers of superior properties for the application in particular in the dental field. Here, an improved adhesion and/or an improved etching function and/or an adaptation of the optical properties for the cosmetic appearance are especially relevant. To provide a remedy in this context is the object of the present invention.

SUMMARY OF THE INVENTION

As a solution to this object, compounds are provided which comprise at least three functionalities, namely (a) a sulfonic acid or sulfonate group of the formula —$(O)_d$—$SO_3M$, with d=0 or 1 and with M=hydrogen or a monovalent metal cation or the corresponding portion of a multivalent metal cation, for a very good etching effect, (b) a (meth)acryl residue as an organically polymerizable group by which the material can be cured after the application on or in the tooth, as well as (c) either (c1) at least one further (meth)acryl residue or an inorganically condensable group in order to enable an especially good crosslinking of the dental material, and/or (c2) a further acid function to improve the etching effect of the molecule, and/or (c3) a function by which the refractive index of a material made from the compounds increases, which leads to an improved translucence and thus an improved adaptation to the tooth color. The acid function according to (c2) can be an additional sulfonic acid group or sulfuric acid group; alternatively, another acidic group can be present, for example, a carboxylic acid group.

Compounds which contain (a) a sulfonate group, (b) an acryl group or a methacryl group and (c) a silyl group are excluded preferably from the invention in case that these compounds contain a trivalent nitrogen atom and each of the three groups (a), (b), and (c) is bonded to another substituent of the nitrogen atom, provided that the (meth)acryl group is coupled as (meth)acrylamide or the acryl group is coupled to the nitrogen atom by the methyl group coupled as a substituent at C2, in particular when the sulfur atom of the sulfonate group is separated by three or four carbon atoms from the nitrogen atom. Above all, the three following compounds, which are disclosed in DE 102 06 451 A1 and U.S. Pat. No. 7,041,709 without these publications indicating a possibility for producing them, should optionally not be encompassed by the invention:

$(RO)_3Si(CH_2)_3N[(CH_2)_xSO_3Na][C(O)C(CH_3)=CH_2]$ with $x=3$ and $x=4$ and

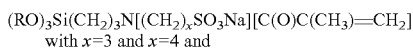

OR] wherein the substituents R in each case, independently of each other, are hydrogen, a substituted or unsubstituted alkyl group with 1 to 20 carbon atoms, a substituted or unsubstituted alkylene or alkenyl group, optionally containing a cyclic structure, with 2 to 20 carbon atoms, a substituted or unsubstituted alkylaryl group, a substituted or unsubstituted arylene or aryl group, or a substituted or unsubstituted hetero arylene or hetero aryl group, in each case with 5 to 20 carbon atoms.

The inventors have succeeded in discovering ways for the preparation of compounds which comprise organically polymerizable groups, in particular (meth)acryl groups, as well as sulfate or sulfonate groups and which are characterized by at least one additional group, selected from a further (meth) acryl residue, an inorganically condensable silyl residue, and a further acid function. Instead of the additional group, or also in addition however, the compounds can have a thioether group by which the refractive index of dental materials made from the compounds increases.

In a first embodiment of the invention, the compounds according to the invention are silanes which can be represented by the following formula (I):

$$R^7_a R^2_b SiZ_{4-a-b} \quad (I)$$

wherein $R^7$ is a hydrolytically (i.e. under hydrolysis conditions) condensable residue; $R^2$ an alkyl, aryl, arylalkyl, alkylaryl or alkylarylalkyl that is substituted or unsubstituted, straight chain, branched or has at least one cyclic structure, as an exception it can be instead a corresponding alkenyl or can encompass an alkenyl whose carbon chain in all cases optionally can be interrupted by —O—, —S—, —NH—, —S(O)—, —C(O)NH—, —NHC(O)—, —C(O)O— —C(O)S, —NHC(O)NH— or C(O)NHC(O) groups which can optionally be oriented in both possible directions; Z is a residue in which are present at least one (meth)acryl group and at least either a sulfonate group or a sulfate group that are bonded directly or indirectly by an unsubstituted or substituted hydrocarbon group to the silicon atom; a is 1, 2 or 3; b is 0, 1 or 2; and a+b together are 2 or 3.

As a result of the suggested preparation methods according to the invention, silanes of the formula (I) are preferred in which, when a sulfonate group is bonded by an alkylene group interrupted by one or several nitrogen atoms to the silicon atom, either no more than two carbon atoms exist between the sulfonate group and the nearest nitrogen atom or, instead, this alkylene group is interrupted by at least one —O—, —S—, —NH—, —C(O)NH—, —NHC(O)—, —S(O)— or —C(O)O— group.

The structures of these new silanes are shown in abstraction in the two following schematic drawings. The alkoxysilane part (present k times, i.e. more than one silyl residue can be present in the molecule which can be the case, e.g., in case of a compound in which two or more (meth)acrylic acid residues are organically linked with each other and are bonded in the indicated manner to an Si atom, respectively) can be used as usual within the scope of the sol gel process generally used for the preparation of silicic acid (poly)condensates for building the inorganic oligomer or polymer structure. In the present case, the latter can also have, as is known from the prior art, the form of dimeres, chains, rings, ladders (i.e. two-dimensional surfaces) or three-dimensional spatial structures, as a function of the number of the hydrolytically condensable residues and the respective hydrolysis conditions. The organically polymerizable molecule part consisting of a variable number m of double bonds in $R'_6$ which are bonded to the silane part can be used for building an additive organic network. The linking unit is of organic nature and variably in length, structure and composition. All molecule parts can be used for modification of the properties.

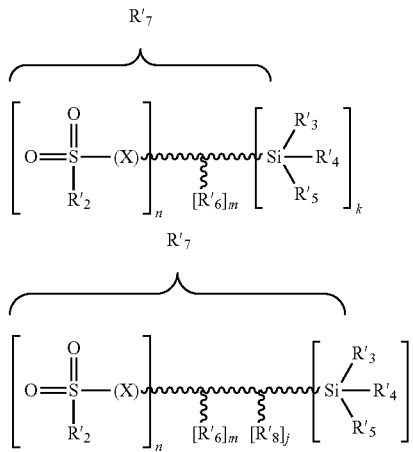

In this context, the groups and indices have the following meaning:

$R'_2$ is OH or a salt —OM with M=a monovalent metal cation or the corresponding portion of a multivalent metal cation, preferably selected from alkali and alkaline earth cations, in particular Na, K, ½ Ca, ½ Mg, or ammonium, X means oxygen or is not present, $R'_3$, $R'_4$, $R'_5$ are either residues which can be subjected with formation of Si—O—Si bridges to a hydrolytic condensation, such as OH, —OR, halogen, e.g., Cl, or residues which are bonded by a carbon atom to the silicon atom; in the simplest case the latter is methyl, $R'_7$ defines the organic residue which has the sulf(on)ate group as well as the double bond-containing residue; the latter is bonded by a carbon atom to the silicon.

$R'_6$ is a double bond-containing residue, usually a (meth)acryl residue.

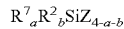 refers to an organic residue which is interrupted as a result of the selected reaction control generally at least by one linking group or an oxygen atom, a sulfur atom, or a secondary or tertiary amino group. As linking groups, in the present case primarily —C(O)O— and —C(O)NH— groups are used; instead, however, also —NHC(O)—, —NHC(O)O—, —C(O)NHC(O)—, —NHC(O)NH— —S(O)— or the corresponding sulfur-containing groups can serve as links.

R'$_8$ means —CO$_2$H or OH.

n, m and j mean in each case at least 1, but can be in certain cases 2 or 3 or even an even higher value.

In a second embodiment of the invention, the compounds according to the invention can be represented by the following formula (II):

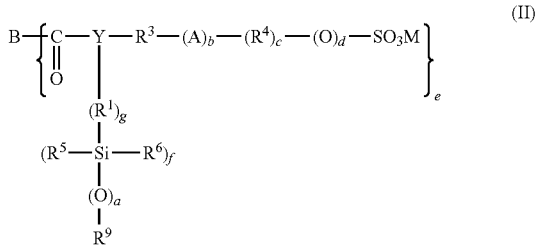

wherein

R$^1$ is a bivalent hydrocarbon residue which, provided that f=1, is bonded by a carbon atom to the silicon atom, R$^9$ is H or alkyl and, in addition, in case of a=0, f=1, and g=1, can be a hydrolytically condensable residue other than alkoxy or

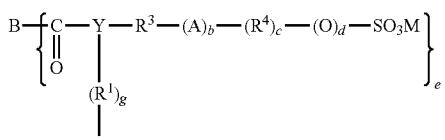

R$^3$ is an alkylene that is unsubstituted or substituted with a functional group, straight chain, branched or has at least one cyclic structure, A is a linking group, R$^4$ is a hydrocarbon group that is optionally interrupted by O, S, NH or NR$^8$ and/or optionally functionally substituted, preferably is an alkylene of this type, M is hydrogen or a monovalent metal cation or the corresponding portion of a multivalent metal cation, preferably selected from alkali and alkaline earth cations, in particular Na, K, ½ Ca, ½ Mg, or ammonium, R$^5$ and R$^6$, independently of each other, are either residues that are condensable under hydrolysis conditions or alkyl, aryl, arylalkyl, alkylaryl or alkylarylalkyl, substituted or unsubstituted, straight-chain, branched or having at least one cyclic structure, in exceptions, however, they can also be a corresponding alkenyl, arylalkenyl or alkenylaryl instead, R$^8$ is alkyl or alkenyl with preferably 1 to 6 or 2 to 6 carbon atoms or a (meth)acryl residue, B is vinyl, 2-allyl or, in case of e>1, an organic residue with e vinyl groups that are present in each case bonded to a group located in the curly brackets, Y is a nitrogen atom, —O—CH=, —S—CH= or —NH—CH=, wherein in each case the oxygen atom, the sulfur atom or the NH group has a bond to the adjacent C(O) group, a is =0 or 1, b is =0 or 1, c is =0 or 1, d is =0 or 1, e is =1, 2 or 3 f is =0 or 1 and g is =0 or 1, wherein then, when f is =1, a and g both are ≠0, and wherein, when f=0, then at least one of the residues R$^3$ or R$^4$ carries a functional substituent which has a (meth)acrylate residue or an acidic group or R$^4$ is an alkylene that is interrupted at least by S.

In a specific variant of the second embodiment, when in the formula (II) Y is a nitrogen atom, b=0, c=0, and preferably also d=0, the residue R$^3$ must be an optionally substituted ethylene, and likewise, when Y is a nitrogen atom, b=0, c=1 and preferably also d=0, the residue R$^4$=an alkylene that is interrupted by O, S, NH or NR$^8$ and optionally functionally substituted.

When f and also g are =0, then a is preferably also 0.

In several preferred embodiments, the silanes according to the invention of the formulae (I) or (II) can be represented by the following formula (Ia):

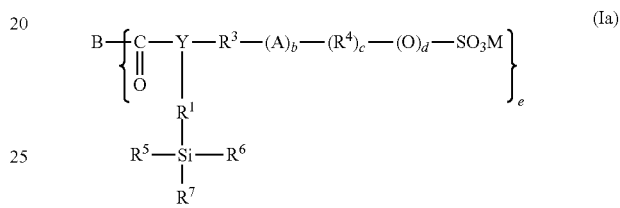

wherein

R$^1$ is a hydrocarbon group as defined above bonded by a carbon atom to the silicon atom, R$^7$ is a hydrolytically condensable residue, and the residues R$^3$, R$^4$, R$^5$, R$^6$, B and Y as well as the indices b, c, d, and e are the same as defined for formula (II).

In a specific variant of the formula (Ia), when in the formula (II) Y is a nitrogen atom, b=0, c=0 and preferably also d=0, then the residue R$^3$ must be an optionally substituted ethylene, and also, when Y is a nitrogen atom, b=0, c=1 and preferably also d=0, then the residue R$^4$=alkylene that is interrupted by O, S, NH or NR$^8$ and optionally functionally substituted.

According to the above formulae, the sulf(on)ate residue or residues as well as the (meth)acryl residue or residues can be bonded directly or indirectly to the hydrocarbon group that is comprised at least of R$^1$. In the terminology of the invention, the expression "directly" is to be understood such that the aforementioned residues are bonded to the silicon without further interruptions of the carbon chain of the alkyl group by S, O, NH or a coupling group. "Indirectly" means accordingly that these residues are coupled to components of the molecule, wherein between them and the alkyl group bonded to the silicon the aforementioned atoms or groups are present, as is evident, e.g., for the residue SO$_3$M in formula Ia for the case that b=1 is or that c=1 with R$^4$ being a group interrupted by O, S, NH or NR$^8$.

The bivalent hydrocarbon residue R$^1$ can be in all embodiments of the invention an alkylene group, an arylene group or a group which has alkylene as well as arylene units. The alkylene group can be straight-chain or branched and/or have at least one cyclic component. In this context, the group can be bonded by an alkylene carbon atom or by an arylene carbon atom to the silicon atom. It is unsubstituted or unsubstituted, and it can be interrupted by one or several oxygen atoms, sulfur atoms, ester groups, amino groups or amide groups.

The linking group A in the formulae (Ia) and (II) is preferably selected from (read from the left to the right in the formulae Ia and II) C(O)NH, NHC(O), NR$^8$C(O), C(O)O and OC(O) and R$^8$ is defined as above. In exceptions, the linking group A can also be selected additionally from NHC(O)O, NR$^8$C(O)O, NHC(O)NH, C(O)NHC(O) and —C(O)S—. The residue R$^4$ in these formulae is substituted in specific embodiments with at least one hydroxyl group and/or with a residue R$^9$COOM wherein R$^9$ is a chemical bond or a C$_1$-C$_6$ alkylene residue and M is hydrogen or the corresponding portion of a multivalent metal cation, preferably selected from alkali and alkaline earth cations, in particular Na, K, ½ Ca, ½ Mg, or ammonium. The aforementioned variants can be realized independently or in combination.

Residues R$^7$ in formula (I) as well as residues R$^5$ and/or R$^6$ in the formulae (Ia) and (II) which can condense under hydrolysis conditions are referred to as inorganic network formers because through them, by hydrolytic condensation reaction, a silicic acid polycondensate network is formed. A person of skill in the art knows accordingly with which number of these residues which oligomer or polymer structure is obtainable and which meaning they can have. Preferably R$^5$ and R$^6$ are OH or a C$_1$-C$_{10}$ alkoxy group, more preferred a C$_1$-C$_4$ alkoxy group, and particularly preferred methoxy or ethoxy. R$^7$ can have the same meaning as R$^5$ and/or R$^6$. However, R$^5$, R$^6$ and R$^7$ can be, as needed, independently of each other, also a halide such as Cl, hydrogen, acyloxy with preferably 2 to 5 carbon atoms, alkylcarbonyl with preferably 2 to 6 carbon atoms or alkoxycarbonyl with preferably 2 to 6 carbon atoms. In some cases, they can have, instead, the meaning NR$^2$ with R$^2$ being hydrogen, alkyl with preferably 1-4 carbon atoms, or aryl with preferably 6-12 carbon atoms.

The expression "sulf(on)ate" encompasses the sulfonate group and the sulfate group. The expressions "sulfonate group" and "sulfate group" encompass the respective acids and salts.

The word or the word part "(meth)acryl . . . " is meant to encompass the respective methacryl and acryl compounds alike. The (meth)acryl residues can be in particular a component of a (meth)acrylic acid ester, (meth)acrylic acid thioester or (meth)acrylic acid amide. Compared with the other (meth) acryl residues, (meth)acrylic acid amide residues are preferred because of their better resistance to hydrolysis.

One aspect of the invention resides in that, for building the chemical structures of the compounds (II), an easy incorporation of the (meth)acryl groups can be achieved in that the latter are reacted in the form of the free acid or an activated acid. This has the result that the (meth)acryl group is incorporated as (meth)acrylic acid ester, amide or thioester in the structures.

With few exceptions, the syntheses are controlled such that a C═C double bond is available for the addition of the sulfonic acid group or sulfate group to the molecule that already contains a (meth)acryl group. As needed, to said double bond either sodium sulfite or a sulfonic acid with a residue that is easily reacted by addition, such as thio or aminoalkane sulfonic acid, can be added. Alternatively, the attachment of the sulfonic acid group can also be carried out by the reverse principle in that thio or aminoalkylsilane or a corresponding silane-free compound is reacted with an alkylene sulfonic acid. With this process, a chain length extension by the carbon atoms of the alkylene group is of course inevitable, which is the reason why the first variant is preferred over the second. Finally, there is still the possibility to cause ring opening of a reactive or strained hetero ring, in particular of a three-membered ring, by sulfite or a hydroxyl, thio or aminoalkane sulfonic acid. This variant has the advantage that the ring opening reaction generates a further reactive group which can be used for the subsequent attachment of the activated (meth) acrylic acid. The hetero ring can be opened alternatively also by means of a sulfate; in these cases, a sulfate group-containing product is obtained.

As mentioned above, an embodiment of the invention concerns silanes of the formulae (Ia) or (II) with f=1 and g=1. As a result of the suggested preparation methods according to the invention, those silanes are preferred herein which, when a sulfonate group is bonded by an alkylene group interrupted by one or several nitrogen atoms to the silicon atom or to the (optionally nearest) (meth)acryl group, either no more than two carbon atoms are present between the sulfonate group and the nearest nitrogen atom or, instead, this alkylene group is interrupted by at least one —O—, —S—, —NH—, —C(O) NH—, —NHC(O)— or —C(O)O group.

All together, for the preparation of silanes with the formula (I), (Ia) or (II) with f=1, four basic variants are available according to the invention as follows:

Variant (A):
(a) a silane with a hydrocarbon group bonded by a carbon atom to the Si atom is provided which carries at least two functional groups, selected from primary amines, secondary amines, hydroxyl groups and thiol groups,
(b) a first one of the two functional groups is reacted with optionally activated (meth)acrylic acid and the second one of the two functional groups is reacted with an optionally activated second carboxylic acid having a C═C double bond and optionally at least one further functionality, and
(c) subsequent to the afore mentioned reaction, a sulfonate group-containing or sulfate group-containing compound or a sulfite is added to the C═C double bond of the carboxylic acid residue reacted with the second functional group in such a way that at the (meth)acryl residue reacted with the first one of the two functional groups such an addition does not take place, which can be ensured in different ways, e.g., by the molar ratio of the groups reacted with each other, wherein the second carboxylic acid having a C═C double bond can be a (meth)acrylic acid or another double bond-containing carboxylic acid.

Purely in exemplary fashion, several possible aminosilanes will be mentioned which can be used in step (a) as a starting material:
(aminoethylaminomethyl)phenylethyl trimethoxysilane, N-(2-aminoethyl)-3-aminopropyl methyldimethoxysilane, N-(2-aminoethyl-3-aminopropyl)trimethoxysilane, N-2-aminoethyl-3-aminopropyl tris(2-ethylhexoxy)silane, 6-(aminohexylaminopropyl)trimethoxysilane, N—(N'-(2-aminoethyl)aminoethyl)-3-aminopropyl trimethoxysilane, N—(N'-(2-aminoethyl)aminoethyl)-3-aminopropyl methyldimethoxysilane, N—(N'-(2-aminoethyl)aminoethyl)-3-aminopropyl triethoxysilane, N—(N'-(2-aminoethyl)aminoethyl)-3-aminopropyl-methyldiethoxysilane, N—(N'-(2-aminoethyl)aminoethyl)-3-aminopropyl trimethylsilane, N—(N'-(2-aminoethyl)aminoethyl)-3-aminopropyl tris (methoxyethoxyethoxy)silane.

Instead, comparable compounds with corresponding hydroxyl or thiol groups could be used. These are disclosed, for example, in EP 0 779 890 A1. Also, the hydrocarbon group can have a configuration other than that shown in the examples shown above.

Variant (B):
(a) a silane with a hydrocarbon group bonded by a carbon atom to the Si atom is provided which carries at least one reactive hetero ring, selected from the three-membered rings oxacyclopropyl (=epoxy), azacyclopropyl, and thiocyclopropyl, and from cyclic carbonates (the latter can be obtained by reaction of an epoxy ring with CO$_2$, but also by other pathways, as disclosed in DE 44 23811 in detail), (b) the hetero ring is reacted with a sulfite or a sulfate or a sulfonate group-containing or a sulfate group-containing compound, and
(c) at least the OH, SH or $NH_2$ group that is obtained in this way is reacted with (meth)acrylic acid that is optionally activated.

Purely in an exemplary fashion, several possible epoxy compounds will be mentioned which can be used in step (a) as a starting material:

Glycidoxymethyl trimethoxysilane, glycidoxymethyl triethoxysilane, 2-glycidoxyethyl trimethoxysilane, 2-glycidoxyethyl triethoxysilane, 3-glycidoxypropyl trimethoxysilane, 3-glycidoxypropyl triethoxysilane, 3-glycidoxypropyl triacetoxysilane, 4-glycidoxybutyl trimethoxysilane, 4-glycidoxybutyl triethoxysilane, glycidoxymethyl(methyl) dimethoxysilane, glycidoxymethyl(ethyl)dimethoxysilane, glycidoxymethyl(phenyl)dimethoxysilane, glycidoxymethyl (vinyl)dimethoxysilane, glycidoxymethyl(dimethyl)methoxysilane, 2-glycidoxyethyl(methyl)dimethoxysilane, 2-glycidoxyethyl(ethyl)dimethoxysilane, 2-glycidoxyethyl (dimethyl)methoxysilane, 3-glycidoxypropyl(methyl) dimethoxysilane, 3-glycidoxypropyl(ethyl)dimethoxysilane, 3-glycidoxypropyl(dimethyl)methoxysilane, 4-glycidoxybutyl(methyl)dimethoxysilane, 4-glycidoxybutyl(ethyl) dimethoxysilane, 4-glycidoxybutyl(dimethyl)methoxysilane, bis-(glycidoxymethyl)dimethoxysilane, bis-(glycidoxymethyl)diethoxysilane, bis-(glycidoxyethyl) dimethoxysilane, bis-(glycidoxyethyl)diethoxysilane, bis-(glycidoxypropyl)dimethoxysilane, bis-(glycidoxypropyl) diethoxysilane, tris-(glycidoxymethyl)methoxysilane, tris-(glycidoxymethyl)ethoxysilane, tris-(glycidoxyethyl) methoxysilane, tris-(glycidoxyethyl)ethoxysilane, tris-(glycidoxypropyl)methoxysilane, tris-(glycidoxypropyl) ethoxysilane, glycidylmethyl trimethoxysilane, glycidylmethyl triethoxysilane, 2-glycidylethyl trimethoxysilane, 2-glycidylethyl triethoxysilane, 3-glycidylpropyl trimethoxysilane, 3-glycidylpropyl triethoxysilane, 3-glycidylpropyl tri(methoxyethoxy)silane, 3-glycidylpropyl triactoxysilane, 3,4-epoxycyclohexylmethyl trimethoxysilane, 3,4-epoxycyclohexylm ethyl triethoxysi lane, 3,4-epoxycyclohexylethyl trim ethoxysilane, 3,4-epoxycyclohexylpropyl trimethoxysilane, 3,4-epoxycyclohexylbutyl trimethoxysilane.

Instead, comparable compounds with corresponding azacyclopropyl and thiocyclopropyl groups could be used. Also, the hydrocarbon group can have a configuration other than that shown in the examples shown above.

Variant (C):
(a) a silane with a hydrocarbon group bonded by a carbon atom to the Si atom is provided which has an amino group or a mercapto group,
(b) an alkenyl sulfonate or a sulfone is reacted with the amino group or the mercapto group, and
(c) the secondary amino group or thio group produced in b. is reacted with (meth)acrylic acid that is optionally activated.

Purely in an exemplary fashion, several possible aminosilanes which can be used in step (a) as a starting material will be mentioned:
4-aminobutyl dimethylmethoxysilane, 4-aminobutyl triethoxysilane, aminomethyltrimethylsilane, aminophenyl trimethoxysilane, 3-(1-aminopropoxy)-3,3-dimethyl-1-propenyl trimethoxysilane, 3-aminopropyl diethylmethylsilane, 3-aminopropyl tris(methoxyethoxyethoxy)silane, 3-aminopropyl dimethylethoxysilane, 3-aminopropyl methyldiethoxysilane, 3-aminopropyl triethoxysilane, 3-aminopropyl trimethoxysilane, 3-aminopropyl tris(trimethylsiloxy)silane, and ω-aminoundecyl trimethoxysilane.

Variant (D):
(a) a (meth)acrylsilane with at least two (meth)acryl groups which are bonded by a carbon atom of a hydrocarbon group to the silicon atom is provided or produced according to the prior art, e.g., according to DE 44 16 857, and
(b) a sulfonate group-containing or sulfate group-containing compound or a sulfite is added in less than stoichiometric quantity to the C=C double bond of one or several of the (meth)acryl residues such that such an addition does not occur on at least one (meth)acryl residue in the molecule, which can be ensured in different ways, e.g., by the molar ratio of the groups reacted with each other.

In the variants (A), (B) and (D), the sulfonate group-containing or sulfate group-containing compound contains preferably OH—, SH— or $NHR^{10}$ group with $R^{10}$=hydrogen or $C_1$-$C_6$ alkyl. Examples of mercapto group-containing sulfonates are straight-chain or cyclic alkane sulfonate or aryl sulfonates, e.g., mercaptoethanesulfonate, mercaptobutanesulfonate, mercaptocyclohexylsulfonate or mercaptobenzenesulfonate. Their sodium salts are common.

A third embodiment of the invention concerns compounds of the formula (II) with f=0 and g=0 wherein at least one of the residues $R^3$ or $R^4$ (the latter in case of c=1) carries a functional substituent which has a (meth)acryl residue and/or an acidic group or—in some cases—instead, or in addition, a thioether group. In this context, the functional substituent can be the (meth)acryl residue or the acidic group or can be a unit comprising this residue/these residues.

To produce purely organic compounds, the above variants (A), (B) and (D) can be modified in a suitable manner in that corresponding compounds without silyl residue are used as starting materials. Concerning the preparation variant (A), it should be noted that compounds according to the invention are obtained when at least three double bond-containing acids are bonded to the starting material which can be realized, e.g., in that a hydrocarbon-containing starting compound has at least three of the functional groups mentioned in (A)a. When to these three groups (meth)acryl residues are attached, a sulfonate group-containing or sulfate group-containing compound or a sulfite can be added either to one of them or to two of them. Compounds according to the invention are obtained also when a starting material with only two functional groups is used wherein, however, at least one of them is reacted with the anhydride of a double bond-containing dicarboxylic acid. With reactions analogous to variant (B), compounds according to the invention are obtained when the hetero ring is reacted with a sulfonate group-containing or sulfate group-containing compound such that another linking site for binding an additional (meth)acrylate or a further acid is generated, i.e. when, e.g., an aminoalkane sulfonate is reacted with the three-membered ring. An organic compound with at least three (meth)acryl groups is used instead of a (meth)acrylsilane in variant (D), for example, trimethylolpropane triacrylate. The sulfur-containing compound can be added in a molar ratio such that the product contains either at least two (meth) acryl residues or at least two sulf(on)ate residues. When in the variants (A), (B) or (D) a thioalkane sulf(on)ate is used, a thioether group is generated which can be considered in some embodiments as the third functional group aside from the at least one (meth)acrylate and the at least one sulf(on)ate group because it increases the refractive index of the condensate producible from it, as explained above.

Inasmuch as in the preparation methods of the invention activated carboxylic acids are to be used, the activation can be done according to common methods; thus, for example, acid chlorides or (intramolecular or intermolecular) anhydrides can be used.

Inasmuch as in the reactions of the invention inorganic sulfonates or sulfates are used, alkali, alkaline earth and ammonium salts are suitable in particular for this purpose. Among the alkali salts, those of sodium and potassium and, among alkaline earth salts, those of magnesium and calcium are preferred. The silanes according to the invention can comprise these salt groups or the corresponding free acid function.

The different reactions according to variant (A) will be explained below in an exemplary fashion with the aid of the reactions 1, 2, and 7 in more detail, wherein the reactions 1 and 2 show the preparation of silane compounds and reaction 7 the preparation of a compound free of silicon. In this context, reaction 7 follows the scheme of reaction 2.

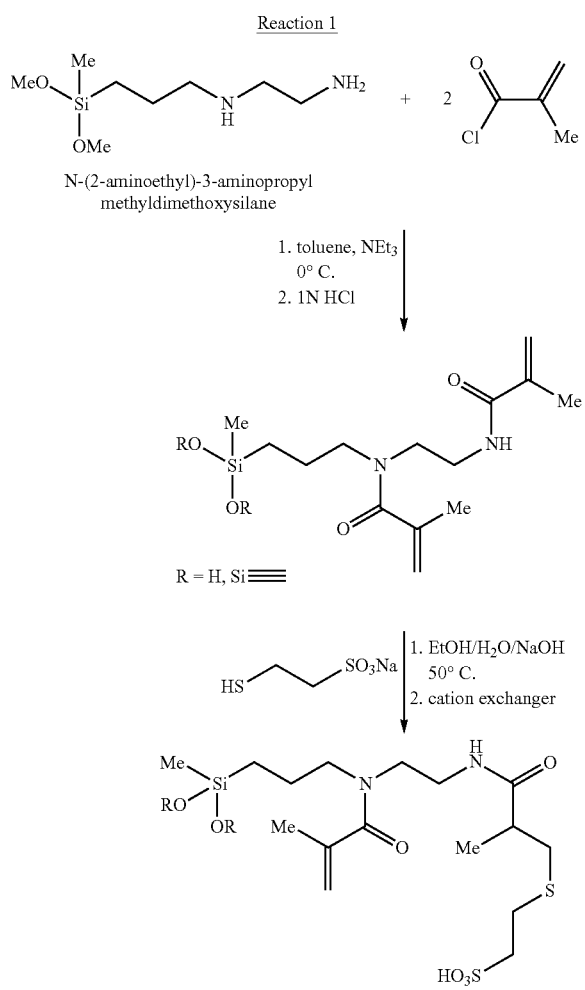

For reaction 1, a starting silane with a hydrocarbon group which carries two amino functions was selected. The reaction occurs in a comparable manner when instead of the primary terminal amine a hydroxyl or a thiol group is present. The secondary NH group could be absent; instead, the alkylene group bonded to the silicon could have a continuous carbon skeleton which would be substituted at a suitable site (e.g., at the position in which in the example the secondary NH group is located) with $NH_2$, OH or SH. The starting silane can have optionally additionally a second secondary amino group; in this case not only two, but three acrylamide groups would be generated by the reaction with methacryloyl chloride.

The length and the structure of the hydrocarbon group in the molecule is not critical and can be selected arbitrarily. Thus, the hydrocarbon can be alkyl that is straight-chain or branched or can have at least one cyclic structure. Moreover, the hydrocarbon can optionally be substituted with other groups which do not take part in the reactions, or can be interrupted arbitrarily by hetero atoms or linking groups.

The substituents of the silicon indicated in reaction 1 by Me and OR can be selected, as needed, arbitrarily, i.e., a suitable number of hydrolytically condensable residues or of residues acting as network modifiers (alkyl groups, aryl groups and the like) can be present that is suitable for the desired silicic acid (hetero) polycondensate. In special embodiments two hydrocarbon groups that carry the reactive functions according to the invention can be present; the sum of hydrolytically condensable residues and residues functioning as network modifiers is then 2.

A sufficient amount of (activated) (meth)acrylic acid is provided, single-stage or two-stage, for the preparation of the silanes according to the invention so that a molecule with two (meth)acrylic acid amide residues is produced. Should the starting silane contain one or two hydroxyl or thiol groups instead of one or two amino groups, in each case the corresponding (meth)acrylic acid esters or (meth)acrylic acid thioesters would be formed. When the starting silane contains a further primary amino group instead of the secondary amino group, a compound with two primary (meth)acrylamides is produced.

In the second step of the reaction, one of the two double bonds introduced by binding of the (meth)acrylic acid group in the molecule is used for a thiol-ene addition. With this reaction, a sulfonic acid group is introduced into the molecule. In a comparable manner, a sulfate group can be introduced.

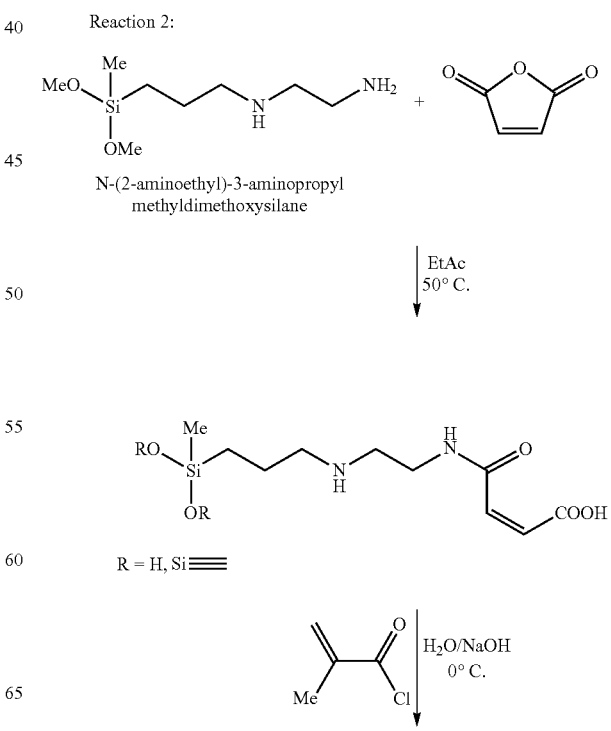

Concerning the employable starting compounds for reaction 2, what has been said in regard to reaction 1 applies. The reaction control differs from reaction 1 in that in a first step it is not (meth)acrylic acid, but another, optionally activated carboxylic acid that is being used which has a C=C double bond, preferably in combination with a C=O group (i.e. a Michael system containing the structure C=C—C=O). In the example, the anhydride of maleic acid was used. The latter, on account of the somewhat different reactivity of the primary and the secondary amino groups, binds surprisingly exclusively to the primary amino group provided that it is not used in excess; the carboxylic acid group that is released in this reaction is not reactive enough to attack at the secondary amino group so that exclusively, or almost exclusively, a product is produced as shown in the reaction in an exemplary way. The latter is reacted afterwards with activated (meth) acrylic acid. Finally, with the aid of sodium sulfite, a sulfonate group can be added to the double bond of the maleic acid residue which can be converted, as needed, in a known manner into a sulfonic acid group.

The product carries, in addition, a free carboxylic acid group which can be used either for an even more improved adhesive and etching effect or, as needed, can be reacted further, e.g., complexed.

This reaction is particularly characterized in that, by selecting the index n, the ratio of (meth)acryl groups to sulfonic acid groups and carboxylic acid groups can be adjusted as needed.

A reaction according to variant (B) will be explained below in an exemplary fashion with the aid of the reaction 5 in more detail.

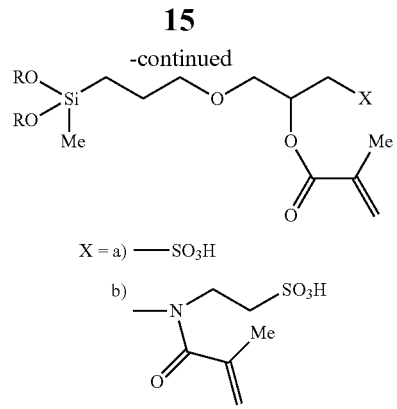

X = a) —SO₃H b) 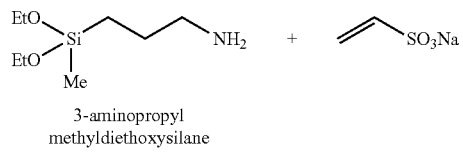

Concerning the variability of the starting silane, reference is being had to the explanations in regard to the reactions 1 and 2 which apply in a comparable manner also to the reaction 5. Only the presence of a strained and thus reactive hetero ring is mandatory in the hydrocarbon group. In the selected example, this is a terminal epoxy group. However, the reaction could also be carried out, instead, with an aziridine or a thiocyclopropyl group. Then, in the first step an amino or a thiol group would result instead of a free hydroxyl group. However, when instead of a strained three-membered ring a cyclic carbonate is used, the reaction can be carried out only according to the variant b) shown in reaction 5.

When the three-membered ring is reacted directly with a sulfite or a sulfate, an ethylene or ethyleneoxy bridge will be formed mandatorily between the SO₃Na or SO₃H group and the linking site for the subsequent esterification of the hydroxyl group produced in the first step with (activated) (meth)acrylic acid. Incidentally, reaction 5 is an example for the ability to couple also two (meth)acrylate residues to an alkylsilane group. Instead of an aminoalkane sulfonic acid, in all cases a thio or a hydroxyalkane sulfonic acid can also be used in reaction 5, by the way. When a thio or hydroxyalkane sulfonic acid is used, there is however no binding of a second methacrylate residue; rather, the residue which is bonded in the variant b) by the sinuous line-shaped link remains a thio or oxyalkane sulfonate group. Even when (meth)acrylic acid is used in less than stoichiometric quantity, binding of only one (meth)acrylate residue occurs. Binding occurs at the most basic one of the available groups, i.e., at the only one or the most basic amino group, provided the latter is present.

When a thioalkane sulfonic acid is used, a thioether group is produced. A molecule according to the product of reaction 5 with this group, but without silyl residue, can be considered also in conformity with the invention in view of some aspects.

A reaction according to variant (C) will be explained below in an exemplary fashion with the aid of the reaction 6 in more detail.

Reaction 6:

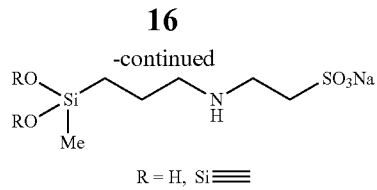

3-aminopropyl methyldiethoxysilane

H₂O/EtOH/NEt₃
80° C.

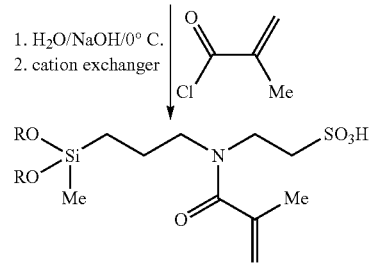

R = H, Si≡

1. H₂O/NaOH/0° C.
2. cation exchanger

Concerning the variability of the starting silanes, reference is being had again to the explanation in regard to the reactions 1 and 2 which apply in a comparable manner also to the reaction 6. The length and other configuration of the alkyl group at the silicon atom can be selected freely, provided it has a primary amino group. To the latter, first an alkenyl sulfonate and afterwards (activated) (meth)acrylic acid are coupled; the sulfonate can be converted, as in the remaining reaction sequences, in a suitable manner into the free sulfonic acid group afterwards.

The preceding reaction examples show reactions to sulfonates. By the use of sulfates instead of sulfites, as disclosed in U.S. Pat. No. 6,777,521, the corresponding sulfate compounds can be obtained in the reactions according to variant (B).

A reaction according to variant (D) will be shown below in an exemplary fashion with the aid of reaction 4:

Reaction 4:

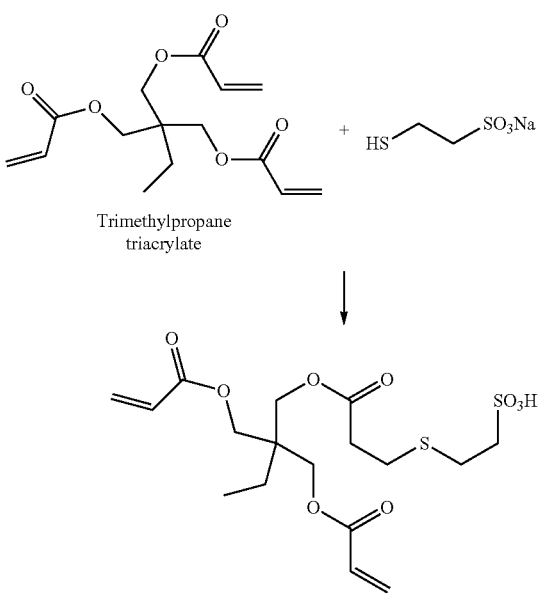

Trimethylpropane triacrylate

This reaction is characterized in that it is possible, by selecting the molar quantity of sulfonic acid compound, to obtain compounds with two (meth)acryl residues and one sulfonic acid residue (when using one mol sulfonic acid compound per one mol of methacrylate) or, when double the molar quantity is used of sulfonic acid compound, compounds with one (meth)acryl residue and two sulfonate residues. When a non-stoichiometric quantity of sulfonate is used, molecule mixtures can be obtained at will.

The preceding reaction examples show reactions to sulfonates. By using sulfates, as disclosed in U.S. Pat. No. 6,777,521, instead of sulfites in the reactions according to variant (B), corresponding sulfate compounds can be obtained.

Inasmuch as the compounds according to the invention are silanes, they can be hydrolytically condensed by usual methods (in particular, the sol gel process); silicic acid polycondensates are produced in this way, also known as ORMOCER®e. These are also encompassed by the invention. The condensation reaction can occur in the presence of additional silanes of the formula $SiR*_a R**_{4-a}$ which are known in the art in very large numbers. $R*$ means herein a hydrolyzable group which enables the incorporation by condensation of the silane into the network, while $R**$ can be any non-condensable residue. When other metal compounds should be additionally present in the condensation reaction, e.g., alkoxy compounds of aluminum, titanium, zirconium or tin, a silicic acid (hetero) polycondensate is generated in which the aforementioned metal atoms are integrated into the Si—O—Si network. $R*$ can be, as needed, a halide like Cl, hydrogen, acyloxy with preferably 2 to 5 carbon atoms, alkylcarbonyl with preferably 2 to 6 carbon atoms, or alkoxycarbonyl with preferably 2 to 6 carbon atoms. In some cases, $R*$ can also be $NR^2$ with $R^2$ being hydrogen, alkyl with preferably 1-4 carbon atoms, or aryl with preferably 6-12 carbon atoms.

It can be desirable to provide additional metal compounds for the incorporation by condensation into the inorganic network. For this purpose, in particular hydrolytically condensable compounds of metals of the main groups III and IV as well as of the transition metal groups III to VI are suitable, e.g., of boron, aluminum, titanium germanium, zirconium or tin. These metal compounds are known in large numbers. In these cases, a silicic acid (hetero) polycondensate is generated in which the afore mentioned metal atoms are integrated into the Si—O—Si network. The additional metal compounds are often alkoxy compounds; in specific embodiments of the invention, the other metal compounds themselves can also have reactive groups however. In this context, of special interest for the present invention are complexes which themselves carry (meth)acryl groups because the latter can be integrated by a subsequent organic polymerization into the organic network.

The reactions and thus the introduction of the sulfonic acid or sulfate groups can be carried out completely or partially at the stage after the polycondensation (usually a sol gel step) instead of at the silane stage, i.e. after building the inorganic polymer structure.

Independent of whether the compounds according to the invention contain silyl groups or not, they can be subjected on account of the available (meth)acryl group(s) to an organic polymerization. The materials resulting therefrom and cured by the polymerization are also encompassed by the invention.

Of course, condensed silanes can also be furthermore cured organically. Materials cured in this way which contain an inorganic Si—O—Si network, optionally with additional cations as mentioned above, as well as a network which has been generated by polymerization of methacryl groups are encompassed by the invention.

The syntheses that can be used according to the invention are characterized by simple reaction control, a low number of working steps, and good yields.

As partially already mentioned above, in specific embodiments of the invention a compound can be substituted with more than one sulfonic acid group or sulfuric acid group and/or with more than one (meth)acryl group. By the presence of more than one (meth)acryl group, the network which forms upon polymerization can become even more finemeshed. In this context, it should be noted that by the contents of polymerizable double bonds the modulus of elasticity of the future organically polymerized polymer can be adjusted in such a way that the polymer becomes more or less flexible and thereby less hard or harder. By the presence of more than one sulfonic acid group or sulfuric acid group, the etching effect of the material is further increased.

The inventors have surprisingly found that already with low sulfonic acid contents an enormous etching effect on the dental tissue can be observed. This can be demonstrated by means of a comparison of the average roughness of the enamel surface: Polished enamel has an average roughness of about 0.21 µm, measured with an optical profilometer of the company UBM. With a phosphonic acid-functionalized silicic acid polycondensate of glycerin-1-methacryloyl-2-(siloxypropyl) carboxymethyl phosphonic acid, roughness in the range of 0.33 µm can be achieved. With condensates of the compounds according to the invention, the roughness is within the range of more than 0.45 µm. Dental enamel images are shown in the FIGS. 1a and 1b.

The compounds according to the invention, namely the silanes as well as the purely organic compounds, are generally water-dissolvable which can be advantageous in many respects. This may have to be expected. Nevertheless, the inventors were surprised of the fact that also the silicic acid polycondensates generated from the silanes are generally water-soluble even though they carry a plurality of (meth)acrylate groups. This has great advantages for many uses wherein medical applications should be mentioned foremost. For the condensates can be applied in aqueous medium, i.e. can be applied in any form without the use of a non-aqueous solvent being required. But also for industrial applications water-based reactions are always advantageous, namely already for reasons of occupational safety and the environmental compatibility.

The possibility of forming further reactive groups in the compounds according to the invention, aside from the sulfonic acid function, opens up additional possibilities. Thus sulfonic acid groups have a stronger etching effect than carboxyl groups, while the latter have complex-forming properties. Provided that additional hydroxyl groups are present, they can be used either for the improvement of wetting of the base surface or for the further reactions which can further modify the compounds according to the invention. One example is complexing or a reaction with a dicarboxylic acid (which can be effected, e.g., with the aid of correspondingly activated acid molecules).

In addition to the degree of polymerization and etching effect, the groups and residues on the compounds of the invention have other properties which are favorably for several applications: The sulfonate or sulfate group is a charge carrier for which reason uses are possible as electrophoresis gels, as materials for the electrophoretic coating or as materials that modify conductivity or antistatic properties. Moreover, the group can serve as an acidic catalyst, namely, on the one hand, for the sol gel process in case of a hydrolytic condensation of the silanes according to the invention (a later separation step for the catalyst separation can then be dispensed with) and, on the other hand, in respect to the future use (an example are the mesoporous membranes with sulfonic acid groups which can serve as catalyst for chemical processes). The group provides furthermore a good solubility in polar media. Particularly for dental purposes, but not exclusively for this purpose, it serves as an adhesion promoting group for inorganic, organic as well as hybrid surfaces. Like carboxylic acid groups, it can also form ionic bonds by means of which e.g., alkali, alkaline earth, ammonium, Ti, Zr, Sn, Ca and other suitable cations can be incorporated in the form of their salts into the polycondensate network. In this way, several modification or material-specific adjustments, e.g., concerning the X-ray opacity, the refractive index or the contact toxicity, can be achieved. The refractive index is moreover influenced (increased) by the presence of a thioether group. By the sulfonate groups or sulfate groups in the material, the material is moreover imparted with an antimicrobial effect. But the invention can be applied also in quite different fields because e.g. proton-conducting membranes, e.g., for fuel cells, can be formed with sulfonate group-containing or sulfate group-containing materials. Further, the materials are suitable e.g. as an ion exchanger, as a pseudo-static phase in the electric-kinetic chromatography or as substances with interfacial tension lowering action (detergent).

In particular by the combination of the sulfonate or sulfate groups and optionally additionally the —$CO_2H$ groups with polymerizable/polyaddition-capable double bonds in a molecule, the compounds lend themselves to the use in the medicine sector (specifically dental field), e.g., as an adhesion promoter and as a matrix component for cements. The adjustment of the refractive index can contribute to the increase of the translucence of the dental material and thus to its approximation to the natural tooth material.

With the functionalized compounds according to the invention, compounds are available which can be used, on the one hand, directly (e.g., for the functionalization of surfaces) and, on the other hand, provided silanes are concerned, can serve as starting compounds for the preparation of inorganic hydrolysates/condensates (resin systems) as well as inorganic/organic composite polymers (matrix systems), i.e. after organic polymerization/polyaddition (curing) with different properties. With the silane-free monomers purely organic polymer materials or polymers can be obtained. By use of any filler materials (particles, fibers), as for example the particles disclosed in DE 1064378, DE 19832965, DE 10018405, DE 1041038 as well as in DE102005018351, corresponding composites are obtained. These plastically processible composites are characterized by very high filler contents that are possible (see nanohybrid composites) in combination with an excellent processibility. Therefore, different properties can be adjusted and matched to the requirements in wide ranges for the compounds according to the invention or the silanes and the resin systems, matrix systems or purely organic polymers as well as the filled systems (composites) obtainable therefrom.

In accordance with the intended special purpose of use, suitable additives can be added to the silicic acid (hetero) polycondensates or the compounds to be organically cured, such as initiators, coloring agents (dyes or pigments), oxidation inhibitors, polymerization inhibitors (for avoiding a premature polymerization), leveling agents, UV absorber, stabilizers, microbiocidal active ingredients or the like, as is known to a person of skill in the art. Examples of polymerization initiators are initiators for radical polymerization, namely for thermal curing like peroxides (e.g., benzoyl peroxide) or photo initiators like benzophenone, camphorquinone or combinations of α-diketones with amine as a reducing agent, as for example disclosed in DE 199 03 177 C2. For the dual curing of radically and cationically polymerizable systems, in particular diaryl iodonium or triaryl sulfonium salts can be added for which the aforementioned publication also provides examples.

A filled dental composite (i.e. an organically not yet crosslinked filled resin of hydrolyzed and condensed silanes according to the invention, after it has been applied for the intended purpose, can be crosslinked in a suitable manner organically and thus be cured. Above all, an organic polymerization of the (meth)acrylate groups is used for this purpose. The silane-free compounds can also be converted by a polymerization of this group into a polymer. This is a radical polymerization that usually occurs with addition of radical starters like the above mentioned ones and optionally known activators, with exposure to e.g. visible light (blue light; dental irradiator), i.e. photochemically, thermally or redox-induced, but also occurs within the scope of 2-component reactions or anaerobically. The combination of self curing action with e.g. photo-induced or thermal curing is also possible.

The use of such materials applies inter alia to the use in the form of bulk materials, composites, cements, adhesives, potting compounds, coating materials, adhesion promoters, binding agents for ceramic particles (ceramic shaping processes), producing or priming of fillers and fibers, use in reaction extruders and the like for most different purposes (in particular for medical, but also for (micro)optical and (micro) electronic applications).

BRIEF DESCRIPTION OF THE DRAWINGS

FIG. 1a shows two REM images at different enlargements of dental enamel roughness produced with a compound according to the invention.

FIG. 1b shows a profilometer image of dental enamel roughness produced with a compound according to the invention.

DESCRIPTION OF PREFERRED EMBODIMENTS

Below, preparation methods for the above reactions are provided in an exemplary way.
Reaction 1:
Stage 1: 5.11 g (0.024 mol) N-(2-aminoethyl)-3-aminopropyl methyldimethoxysilane was dissolved in 5.21 g triethylamine and 30 ml toluene and was cooled to 0° C. Afterwards, 5.0 ml (0.051 mol) methacrylic acid chloride in 30 ml toluene were added dropwise. The reaction mixture was stirred for 3 h at room temperature. The mixture was centrifuged and the obtained solution adjusted for hydrolysis and condensation with 1 N hydrochloric acid to pH 1-2. After 24 h the volatile components were removed under vacuum.

Stage 2: 3.92 g (0.013 mol) of the product of stage 1 were dissolved in 30 ml ethanol, the solution adjusted with sodium hydroxide to pH 10, and heated to 60° C. Afterwards 1.93 g (0.015 mol) sodium 2-mercaptoethansulfonate dissolved in 40 ml $H_2O$ were added dropwise, followed by stirring for 4 h. Ethanol was removed under vacuum and the aqueous solution treated with a cation exchanger. The volatile components were removed under vacuum. The end product is redissolvable in water.
Reaction 2:
Stage 1: 8.69 g (0.042 mol) N-(2-aminoethyl)-3-aminopropyl methyldimethoxysilane were dissolved in 50 ml ethyl acetate and heated to 50° C. A solution of 4.23 g (0.043 mol) maleic acid anhydride dissolved in 30 ml ethyl acetate was added dropwise, followed by stirring for 19 h. The mixture was centrifuged and the residual material purified twice with ethyl acetate and dried under vacuum.

Stage 2: 6.06 g (0.021 mol) of the product of stage 1 were dissolved in 5 ml water and 1.72 g NaOH and cooled to 0° C. 2.1 ml (0.021 mol) methacrylic acid chloride were slowly added dropwise with strong stirring action, followed by stirring for 5 h at 50° C. Afterwards, the volatile components were removed under vacuum.

Stage 3: 9.82 g (0.021 mol) of the product of stage 2 were dissolved in 20 ml water and heated to 60°. Afterwards, 2.61 g (0.021 mol) sodium sulfite were added dropwise with stirring action, followed by stirring for 24 h. The aqueous solution was treated with a cation exchanger and the volatile components were removed under vacuum. The product can be redissolved in water.

Reaction 5:

a)

Stage 1: 5.04 g (0.040 □mol) sodium sulfite were dissolved in 30 ml H$_2$O and heated to 80° C. A solution of 9.96 g (0.040 □mol) 3-glycidoxypropyl methyldiethoxysilane in 10 ml ethanol was added dropwise, followed by stirring under reflux for 3 h.

After evaporation of ethanol, the aqueous phase was purified with ethyl acetate and afterwards the volatile components were removed under vacuum.

Stage 2: 5.04 g (0.016 mol) of the product of the stage 1 were dissolved in 10 ml water and 2.79 g (0.070 □mol) NaOH and cooled to 0° C. Afterwards, 4.0 ml (0.016 mol) methacrylic acid chloride were added dropwise and the reaction mixture stirred for 4 h at 30° C. The solution was purified with ethyl acetate, the aqueous phase treated with a cation exchanger, and the volatile components removed afterwards under vacuum. The product can be redissolved in water.

b)

Stage 1: 3.38 g (0.027 mol) 2-aminoethane sulfonic acid were dissolved in 40 ml H$_2$O and adjusted with 1 N NaOH solution to pH 14. A solution of 6.81 g (0.027 mol) 3-glycidoxypropyl methyldiethoxysilane in 30 ml ethanol was added dropwise at 50° C., followed by stirring for 3 h. Then ethanol was removed under vacuum and the aqueous solution was purified with ethyl acetate. Afterwards the volatile components were removed under vacuum.

Stage 2: 5.12 g (0.014 mol) of the product of stage 1 were dissolved in 10 ml water and 2.58 g (0.065 mol) NaOH and cooled to 0° C. 1.5 ml (0.016 mol) methacrylic acid chloride were added dropwise and the reaction mixture stirred for 4 h at 30° C. The aqueous solution was purified with ethyl acetate and was treated with a cation exchanger. Afterwards the volatile components were removed under vacuum. The product can be redissolved in water.

Reaction 6:

Stage 1: 5.14 g (0.027 mol) 3-aminopropyl methyldiethoxysilane were dissolved in 30 ml ethanol and 1.65 g (0.016 g) triethylamine and heated to 70° C. Afterwards 14 ml (0.027 mol) aqueous 25% sodium vinylsulfonate solution were added dropwise, followed by stirring for 24 h. Afterwards ethanol was removed under vacuum and the aqueous solution was washed with ethyl acetate. Afterwards the volatile components were removed under vacuum.

Stage 2: 5.73 g (0.018 mol) of the product of stage 1 was dissolved in in 10 ml water and 2.92 g (0.075 mol) NaOH and cooled to 0° C. 1.8 ml (0.018 mol) methacrylic acid chloride were added dropwise and the reaction mixture stirred for 5 h at 30°. Afterwards the solvent was removed under vacuum. The aqueous solution was purified with ethyl acetate and was treated with a cation exchanger. Afterwards the volatile components were removed under vacuum. The product can be redissolved in water.

Reaction 4:

1.50 g (0.005 mol) trimethylpropane triacrylate and 13.9 mg (0.06 wt. %) butylhydroxytoluene were dissolved in 20 ml ethanol and heated to 40° C. 0.87 g (0.005 mol) sodium 2-mercaptoethanesulfonate were dissolved in 20 ml water and added dropwise. The reaction mixture was stirred for 4 h and ethanol was removed afterwards at 40° C. under vacuum. The aqueous solution was purified afterwards with ethyl acetate, treated with a cation exchanger, and the volatile components were removed under vacuum. The product can be redissolved in water.

What is claimed is:

1. A compound comprising:
    a first functionality (a) that is a sulfonate group or a sulfate group of the formula —(O)$_d$—SO$_3$M with d=0 or 1 and with M=hydrogen or a monovalent metal cation or a corresponding portion of a multivalent metal cation;
    a second functionality (b) that is a (meth)acryl residue;
    a third functionality (c1) that is an inorganically condensable silyl group; and
    at least one fourth functionality selected from the group consisting of (c2) a carboxylic acid function and (c3) a function by which the refractive index of a material made from the compound is increased and that is a thioether group.

2. The compound according to claim 1 with the formula (II)

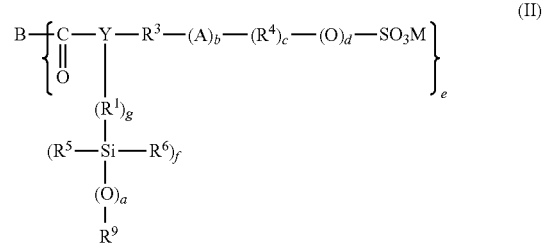

wherein

R$^1$ is a bivalent hydrocarbon residue which is optionally interrupted by one or more oxygen atoms, sulfur atoms, ester groups, amino groups or amide groups and which is bonded by a carbon atom to the silicon atom, R$^9$ is H or alkyl or, in case of a=0 and g=1, a hydrolytically condensable residue or

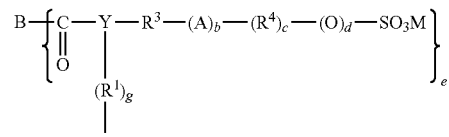

R$^3$ is an alkylene that is unsubstituted or substituted with a functional group, straight-chain, branched or has at least one cyclic structure, A is a linking group, R$^4$ is a hydrocarbon group that is unsubstituted or substituted with a functional substituent and that is optionally interrupted by O, S, NH or NR$^8$, M is hydrogen or a monovalent metal cation or the corresponding portion of a multivalent metal cation, R⁵ and R⁶, independently of each other, are either residues that are condensable under hydrolysis conditions or alkyl, aryl, arylalkyl, alkylaryl or alkylarylalkyl substituted or unsubstituted, straight-chain, branched or having at least one cyclic structure, or a corresponding alkenyl, arylalkenyl, or alkenylaryl, R⁸ is alkyl or alkenyl or a (meth)acryl residue, B is vinyl, 2-allyl or, in case of e>1, an organic residue with e vinyl groups, wherein each one of the e vinyl groups is bonded to one of the e groups defined by the curly brackets, Y is a nitrogen atom, —O—CH=, —S—CH= or —NH—CH=, wherein in each case the oxygen atom, the sulfur atom or the NH group has a bond to the adjacent C(O) group, a is 0 or 1, b is 0 or 1, c is 0 or 1, d is 0 or 1, e is 1, 2 or 3, f is 1, and g is 0 or 1.

3. The compound according to claim 2, wherein at least one of the residues R³ and R⁴ is substituted with a residue R¹⁰COOM and optionally with at least one hydroxyl group and/or a residue SO₃M, wherein R¹⁰ is a chemical bond or a C₁-C₆ alkylene residue.

4. The compound according to claim 2, with the proviso that, when Y is a nitrogen atom, b=0 and c=0, the residue R³ means unsubstituted or substituted ethylene, and, when Y is a nitrogen atom, b=0 and c=1, the residue R⁴ is an alkylene that is unsubstituted or substituted with a functional substituent and that is interrupted by O, S, NH or NR⁸.

5. The compound according to claim 2, wherein the linking group A in the formula (II) is selected from (read from the left to the right in the formula (II)) C(O)NH, NHC(O), NR⁸C(O), C(O)O, and OC(O), wherein R⁸ is alkyl or alkenyl or a (meth)acryl residue.

6. The compound according to claim 1 that is a silane of the formula (I)

wherein

R⁷ is a hydrolytically condensable residue;

R² is an alkyl, aryl, arylalkyl, alkylaryl or alkylarylalkyl that is substituted or unsubstituted, straight-chain, branched or has a cyclic structure or is a corresponding alkenyl whose carbon chain in all cases optionally can be interrupted by —O—, —S—, —NH—, —S(O)—, —C(O)NH—, —NHC(O)—, —C(O)O—, —C(O)S—, —NHC(O)NH—, or C(O)NHC(O) groups which can optionally be oriented in both possible directions;

Z is a residue in which are present at least one (meth)acryl group and either at least a sulfonate group or a sulfate group that are bonded directly or indirectly by an unsubstituted or substituted hydrocarbon group via an Si—C bond to the silicon atom, wherein Z contains the at least one fourth functionality;

a is 1, 2 or 3;

b is 0, 1 or 2; and a+b together are 2 or 3.

7. The compound according to claim 6 with the formula (Ia)

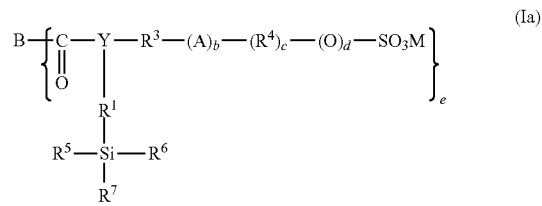

wherein

R¹ is a bivalent hydrocarbon group bonded by a carbon atom to the silicon atom, which is optionally interrupted by one or more oxygen atoms, sulfur atoms, ester groups, amino groups or amide groups, R⁷ is a hydrolytically condensable residue, R³ is an alkylene that is unsubstituted or substituted with a functional group, straight-chain, branched or has at least one cyclic structure, R⁴ is a hydrocarbon group that is unsubstituted or substituted with a functional substituent and that is optionally interrupted by O, S, NH or NR⁸, R⁵ and R⁶, independently of each other, are either residues that are condensable under hydrolysis conditions or alkyl, aryl, arylalkyl, alkylaryl or alkylarylalkyl substituted or unsubstituted, straight-chain, branched or having at least one cyclic structure, or a corresponding alkenyl, arylalkenyl, or alkenylaryl, B is vinyl, 2-allyl or, in case of e>1, an organic residue with e vinyl groups wherein each one of the e vinyl groups is bonded to one of the e groups defined by the curly brackets, Y is a nitrogen atom, —O—CH=, —S—CH= or —NH—CH=, wherein in each case the oxygen atom, the sulfur atom or the NH group has a bond to the adjacent C(O) group, b is 0 or 1, c is 0 or 1, d is 0 or 1, and e is 1, 2 or 3.

8. The compound according to claim 7, with the proviso that, when Y is a nitrogen atom, b=0 and c=0, the residue R³ means optionally substituted ethylene, and, when Y is a nitrogen atom, b=0 and c=1, the residue R⁴ is an alkylene that is unsubstituted or substituted with a functional substituent and that is interrupted by O, S, NH or NR⁸.

9. The compound according to claim 7, wherein the linking group A in the formula (Ia) is selected from (read from the left to the right in the formula Ia) C(O)NH, NHC(O), NR⁸C(O), C(O)O, and OC(O), wherein R⁸ is alkyl or alkenyl or a (meth)acryl residue.

10. The compound according to claim 7, wherein at least one of the residues R³ and R⁴ is substituted with at least a residue R¹⁰COOM and optionally with at least one hydroxyl group and/or with a residue SO₃M, wherein M is hydrogen or a monovalent metal cation or a corresponding portion of a multivalent metal cation, wherein R¹⁰ is a chemical bond or a C₁-C₆ alkylene residue.

11. A method for preparing a compound with the formula (II) as defined in claim 2, the method comprising the steps of:

(a) Providing a hydrocarbon compound which carries at least two functional groups, selected from primary amines, secondary amines, hydroxyl groups and thiol groups;

(b) Reacting a first one of the two functional groups with optionally activated (meth)acrylic acid and reacting the second one of the two functional groups with a carboxylic acid that is optionally activated and has a C=C double bond, wherein said carboxylic acid can be (meth) acrylic acid or a different double bond-containing carboxylic acid; and (c) Adding, subsequent to the step (b), a sulfonate group-containing compound or a sulfate group-containing compound or a sulfite to the C=C double bond of the carboxylic acid residue reacted with said second functional group in such a way that on the (meth)acryl residue reacted with said first functional group such an addition does not take place.

12. The method according to claim 11, wherein the sulfonate group-containing compound or the sulfate group-containing compound has an OH—, SH— or NHR$^{11}$-group, with R$^{11}$=hydrogen or $C_1$-$C_6$ alkyl.

13. A method for preparing a compound of the formula (II) as defined in claim 2, the method comprising the steps of:
(a) Providing a hydrocarbon compound which carries at least one hetero ring, selected from the group consisting of oxacycyc opropyl, azacyclopropyl, thiocyclopropyl, and a cyclic carbonate,
(b) Reacting the hetero ring with a sulfite or a sulfonate group-containing compound or a sulfate group-containing compound, and
(c) Reacting at least the OH—, SH— or NH$_2$-group generated in the step (b) with optionally activated (meth) acrylic acid.

14. The method according to claim 13, wherein the sulfonate group-containing compound or the sulfate group containing compound has an OH—, SH— or NHR$^{11}$-group, with R$^{11}$=hydrogen or $C_1$-$C_6$ alkyl.

15. A method for preparing a compound of the formula (II) as defined in claim 2, the method comprising the steps of:
(a) Providing a hydrocarbon compound which has an alkylamino group or a mercapto group,
(b) Reacting an alkenyl sulfonate with the alkylamino group or the mercapto group, and
(c) Reacting the secondary amino group produced in the step (b) with optionally activated (meth)acrylic acid.

16. A method for preparing a compound of the formula (II) as defined in claim 2, the method comprising the steps of:
(a) Providing an organic compound with at least three (meth)acryl groups, and
(b) Adding a sulfonate group-containing compound or a sulfate group-containing compound, each comprising an SH group, in less than stoichiometric quantity to the C=C double bond of one or several of the (meth)acryl groups such that the addition does not take place at least at one (meth)acryl residue.

17. A method for preparing a compound of the formula (II) as defined in claim 2, the method comprising the steps of:
(a) providing a (meth)acrylsilane with at least two (meth) acryl groups, which are bonded by a carbon atom of a hydrocarbon group to the silicon atom, and
(b) adding a sulfonate group-containing compound or a sulfate group-containing compound, each comprising an SH group, in less than stoichiometric quantity to the C=C double bond of one or several of the (meth)acryl residues such that the addition does not take place at least at one (meth)acryl residue.

18. A silicic acid (hetero) poycondensate produced by a hydrolytic condensation of the compound of claim 2.

19. The silicic acid (hetero) polycondensate according to claim 18, produced by additionally using at least one hydrolytically condensable metal compound of a metal, selected from metals of the main group III and IV and metals of the transition metal groups III to VI.

20. The silicic acid (hetero) polycondensate according to claim 18, wherein the silicic acid (hetero) polycondensate is water-soluble.

21. A silicic acid (hetero) polycondensate produced by a hydrolytic condensation of the compound of claim 6.

22. The silicic acid (hetero) polycondensate according to claim 21, produced by additionally using at least one hydrolytically condensable metal compound of a metal, selected from metals of the main group III and IV and metals of the transition metal groups Ill to VI.

23. The silicic acid (hetero) polycondensate according to claim 21, wherein the silicic acid (hetero) polycondensate is water-soluble.

24. The silicic acid (hetero) polycondensate according to claim 21 in the form of a dental material.

25. A silicic acid (hetero) polycondensate produced by a hydrolytic condensation of the compound of claim 7.

26. The silicic acid (hetero) polycondensate according to claim 25, produced by additionally using at least one hydrolytically condensable metal compound of a metal, selected from metals of the main group III and IV and metals of the transition metal groups III to VI.

27. The silicic acid (hetero) polycondensate according to claim 25, wherein the silicic acid (hetero) polycondensate is water-soluble.

28. A polymerisate, obtained from or by use of at least one compound as defined in claim 1 by polymerization of at least some of the (meth)acryl groups.

29. The polymerisate according to claim 28, comprising an inorganically condensed network of or with Si—O—Si bridges.

30. The polymerisate according to claim 28 in the form of a dental material.

31. A polymerisate, obtained from or by use of at least one compound as defined in claim 6 by polymerization of at least some of the (meth)acryl groups.

32. The polymerisate according to claim 31, comprising an inorganically condensed network of or with Si—O—Si bridges.

33. The compound according to claim 1 of the formula

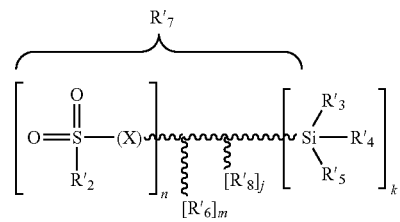

wherein:
R'$_2$ is OH or a salt —OM with M=a monovalent metal cation or the corresponding portion of a multivalent metal cation,
X means oxygen or is not present,
R'$_3$, R'$_4$, R'$_5$ are either residues which can be subjected with formation of Si—O—Si bridges to a hydrolytic condensation or residues which are bonded by a carbon atom to the silicon atom,
R'$_7$ defines the organic residue which has the sulf(on)ate group as well as the (meth)acryl residue, wherein the (meth)acryl residue is bonded by a carbon atom to the silicon, $R'_6$ is a (meth)acryl residue, ⁓⁓⁓ refers to an organic residue which can be interrupted by at least one linking group or an oxygen atom, a sulfur atom, or a secondary or tertiary amino group, wherein the linking groups are selected from the group consisting of —C(O)O—, —C(O)NH—, —NHC(O)—, —NHC(O)O—, —C(O)NHC(O)—, —NHC(O)NH—, —S(O)— and the corresponding sulfur-containing groups, $R'_8$ means —CO or OH, n, m and j mean in each case 1, 2, 3 or a higher value.

34. A silicic acid (hetero) polycondensate produced by a hydrolytic condensation of the compound of claim 1.

\* \* \* \* \*